US007674469B2

(12) United States Patent
Lakshmanan et al.

(10) Patent No.: US 7,674,469 B2
(45) Date of Patent: Mar. 9, 2010

(54) FELINE INFLUENZA VACCINE AND METHOD OF USE

(75) Inventors: Nallakannu P. Lakshmanan, Millsboro, DE (US); Melissa A. Lum, Rehoboth Beach, DE (US); Frank J. Sterner, Belgrade Lakes, ME (US); Frederick Randal Bethke, Millsboro, DE (US)

(73) Assignee: Internet International B.V., Boxmeer (NL)

( * ) Notice: Subject to any disclaimer, the term of this patent is extended or adjusted under 35 U.S.C. 154(b) by 0 days.

(21) Appl. No.: 11/924,243

(22) Filed: Oct. 25, 2007

(65) Prior Publication Data

US 2008/0102086 A1 May 1, 2008

Related U.S. Application Data

(60) Provisional application No. 60/854,351, filed on Oct. 25, 2006.

(51) Int. Cl.
| | |
|---|---|
| *A61K 39/38* | (2006.01) |
| *A61K 39/385* | (2006.01) |
| *A61K 39/295* | (2006.01) |
| *A61K 39/12* | (2006.01) |
| *A61K 39/21* | (2006.01) |
| *A61K 39/125* | (2006.01) |
| *A61K 39/205* | (2006.01) |
| *A61K 39/00* | (2006.01) |
| *A61K 39/235* | (2006.01) |
| *A61K 39/10* | (2006.01) |
| *A61K 39/118* | (2006.01) |
| *A61K 39/02* | (2006.01) |

(52) U.S. Cl. .............. 424/209.1; 424/184.1; 424/193.1; 424/196.11; 424/197.11; 424/201.1; 424/204.1; 424/216.1; 424/229.1; 424/233.1; 424/224.1; 424/207.1; 424/240.1; 424/263.1

(58) Field of Classification Search ....................... None
See application file for complete search history.

(56) References Cited

U.S. PATENT DOCUMENTS

| | | | |
|---|---|---|---|
| 2002/0025325 | A1 | 2/2002 | Chu et al. |
| 2007/0098742 | A1 | 5/2007 | Yoon et al. |
| 2007/0293449 | A1 | 12/2007 | Cui et al. |
| 2008/0075736 | A1 | 3/2008 | Crawford |
| 2008/0107681 | A1 | 5/2008 | Karaca |
| 2008/0107687 | A1 | 5/2008 | Poulet |
| 2008/0187546 | A1 | 8/2008 | Wasmoen et al. |

FOREIGN PATENT DOCUMENTS

| | | | |
|---|---|---|---|
| EP | 1923070 | | 5/2008 |
| WO | WO2006108846 | A1 | 10/2006 |
| WO | WO2006116082 | A1 | 11/2006 |
| WO | WO2007047938 | A2 | 4/2007 |
| WO | 2008059018 | | 5/2008 |

OTHER PUBLICATIONS

Crawford, P. C. et al., "Transmission of Equine Influenza Virus to Dogs," Oct. 21, 2005, Science, 310, p. 482-485.
Songserm, T. et al., "Avian Influenza H5N1 in Naturally Infected Domestic Cat," Apr. 2006, Emerging Infectious Diseases, vol. 12, No. 4, p. 681-683.
Kuiken, T. et al., "Feline friend or potential foe?" Apr. 6, 2006, Nature, vol. 440, p. 741-742.
Jeremijenko, Andrew et al., "Front the front lines," Apr. 6, 2006, Nature, vol. 440, p. 726-727.
"UF Researchers: Equine Influenza Virus Likely Involved in Recent Respiratory Disease Outbreak in Racing Greyhounds," University of Florida News, Apr. 22, 2004.
Gibbs, E.P.J., "Emerging zoonotic epidemics in the interconnected global community," Nov. 26, 2005, The Veterinary Record, 157, p. 673-679.
"Canine Influenza Virus," posted at the Cornell University College of Veterinary Medicine (http://diaglab.vet.cornell.edu/issues/civ.asp), retrieved on Apr. 12, 2006.
Butler, D., "Thai dogs carry bird-flu virus, but will they spread it?" Feb. 16, 2006, Nature, vol. 439, p. 773.
Lewis, David B., "Avian Flu to Human Influenza," 2006, Annu Rev Med, 57, p. 139-154.
"European advice on H5N1 avian influenza in cats," Mar. 11, 2006, The Veterinary Record, p. 314.

"Canine Influenza Backgrounder," posted by AVMA at http://www.avma.org/public__health/influenza/canine__bgnd.asp, retrieved on Nov. 27, 2005.

Troyer, Heather L., Canine Influenza Virus ('Dog Flu'): A Summary of Clinical Caes at The Oradell Animal Hospital, Paramus, New Jersey, Oct. 2005.

Ramanujan, Krishna, "Contagious equine flu virus infecting dogs across U.S. is isolated by Cornell researchers," posted by Cornell University at http://www.news.cornell.edu/stories/Sept05/Dog__Flu.kr.html, retrieved on Nov. 27, 2005.

Von Grotthuss, M. et al, "Influenza Mutuation from Equine to Canine," Mar. 3, 2006, Science, vol. 311, p. 124.
Clark, A., "Canine Influenza Virus Surfaces," Nov. 1, 2005, JAVMA, vol. 227, No. 9, p. 1377-1378.
Hampton, Tracy, "Equine Influenza Jumps to Canines," Oct. 26, 2005, vol. 294, No. 16, p. 2015.
Daly, Janet M., "Equine influenza in dogs: Too late to bolt the stable door?" The Veterinary Journal, vol. 171, p. 7-8 (2006).

Karaca, K. et al., "Immunogenicity of Fowlpox Virus Expressing the Avian Influenza Virus H5 Gene(TROVAC AIV-H5) in Cats." Clinical and Diagnostic Laboratory Immunology, Nov. 2005, p. 1340-1342.

(Continued)

*Primary Examiner*—Robert B Mondesi
*Assistant Examiner*—Benjamin P Blumel
(74) *Attorney, Agent, or Firm*—William M. Blackstone; Aaron L. Schwartz

(57) ABSTRACT

This invention is directed to a vaccine and a method for using the vaccine to protect a feline from influenza virus infection. The vaccine comprises one or more antigens from one or more H3, N8, H7 or N7-type influenza viruses.

6 Claims, No Drawings

OTHER PUBLICATIONS

Payungporn, S. et al.: Influenza A Virus (H3N8) in Dogs with Respiratory Disease, Florida, Emerging Infectious Diseases 14(6):902-908 (2008).

American Veterinary Medical Association, Canine Influenza Backgrounder, Feb. 14, 2007.

Veterinary Advisory: Aug. 12, 2005, Canine Influenza Virus (Canine Flu), College of Veterinary Medicine, Public Relations Office, accessed at www.vetmed.ufl.edu on Jan. 10, 2008.

FELINE INFLUENZA VACCINE AND METHOD OF USE

This application claims priority from U.S. Provisional Application No. 60/854,351 of the same title filed on Oct. 25, 2006, the entire disclosure of which is incorporated by reference in its entirety.

FIELD OF THE INVENTION

This invention relates to vaccines, kits comprising such vaccines, and methods of using such vaccines to protect felines from influenza virus infections.

BACKGROUND OF THE INVENTION

Respiratory infections in animals, characterized by coughing or other symptoms, have been recognized for a long time. Such infections may be particularly common when non-vaccinated animals are housed in high-density circumstances. They are known to be caused by, for example, herpesvirus, calicivirus or influenza viruses, with and without other organisms that can affect or complicate such respiratory infections. Such conditions generally have not been directly mortal, although they can lead to more severe infections and death.

Influenza viruses known to infect one family of animals are not typically capable of infecting other families of animals. However, a respiratory disease has recently been observed infecting racing greyhounds, which resulted in the death of a number of dogs. In January of 2004, Dr. Cynda Crawford reportedly began investigating greyhound deaths at a racetrack in Jacksonville, Fla., where 24 greyhounds contracted the disease and 8 died. Dr. Crawford reported that the dogs, having no natural immunity to the virus, were all infected if they were exposed to the virus, and 80% of the infected dogs developed symptoms. She also reported the virus to be an H3N8 flu, which is closely related to an equine flu strain. See *New York Times.com, Sep.* 22, 2005. See also, Crawford, P. C., et al., "Transmission of Equine Influenza Virus to Dogs," *Science,* 310, pp. 482-85 (Oct. 21, 2005).

U.S. Patent Application No. 60/673,443, filed Apr. 21, 2005 and Ser. No. 11/409,416, filed Apr. 21, 2006, and international patent application no. PCT/US2006/015090, filed Apr. 21, 2006 (published as WO06/116082), (all of which are herein incorporated by reference in their entirety) also describe Dr. Crawford's work with equine influenza viruses that infect canines. U.S. Patent Application No. 60/779,080, filed Mar. 3, 2006 (and herein incorporated by reference in its entirety) describes the use of equine influenza viruses as vaccines against influenza in canines.

There is a need for vaccines and methods for protecting any given species of animal from influenza viruses that can infect other species of animals. The following disclosure describes vaccines and methods that are generally suitable for addressing this need.

SUMMARY OF THE INVENTION

The present invention relates to vaccines and methods for protecting felines from influenza using an H3, N8, H7 or N7-type influenza antigen. The present invention also relates to kits comprising such vaccines, and methods for using such vaccines. This protection includes preventing, reducing the risk of, delaying the onset of, reducing the spread of, ameliorating, suppressing, and/or eradicating the influenza and/or one or more of its symptoms. It is believed that the vaccines, kits, and methods of this invention are generally suitable for use with any member of the Felidae (or, feline) family.

Briefly, this invention is directed, in part, to a method for protecting a feline from an influenza virus infection (i.e., preventing infection within an individual feline, preventing spread of infection from one feline to another feline or other species (e.g. human, canine, equine, poultry), reducing the risk of, delaying the onset of, suppressing, ameliorating, or eradicating an influenza virus infection). The method comprises administering a therapeutically effective amount of a vaccine that comprises at least one H3, N8, H7 or N7-type influenza virus antigen.

This invention also is directed, in part, to a method for protecting a feline from respiratory lesions (i.e., preventing, reducing the risk of, delaying the onset of, suppressing, ameliorating, or eradicating respiratory lesions) caused by influenza virus by administering a composition comprising an H3, N8, H7 or N7-type influenza antigen. The method comprises administering to the feline a therapeutically effective amount of a vaccine that comprises at least one H3, N8, H7 or N7-type influenza virus antigen.

This invention also is directed, in part, to a method for protecting a feline from having influenza virus in nasal or oral secretion (i.e., preventing, reducing the risk of, delaying the onset of, suppressing, ameliorating, or eradicating feline influenza virus in nasal or oral secretion) caused by influenza virus infection by administering to the feline a composition comprising an H3, N8, H7 or N7-type influenza antigen. The method comprises administering to the feline a therapeutically effective amount of a vaccine that comprises at least one H3, N8, H7 or N7-type influenza virus antigen.

The influenza antigen can be delivered to the feline in any manner well known to the skilled artisan. Non-limiting routes of administration include parenteral delivery (including subcutaneous or intramuscular delivery), or other routes such as intradermal or transdermal delivery. Devices for parenteral, intradermal or transdermal delivery are well known to the skilled artisan and can be used with the invention.

One embodiment of the invention is directed to a method for protecting a feline from an influenza virus infection, wherein the method comprises administering to the feline a therapeutically effective amount of a vaccine comprising: i) at least one H3, N8, H7 or N7-type influenza virus antigen and ii) at least one pharmaceutically acceptable excipient. The H3, N8, H7 or N7-type influenza virus antigen(s) can comprise one or more inactivated viruses. The H3, N8, H7 or N7-type influenza virus antigen(s) can comprise one or more from the group consisting of i) one or more live attenuated viruses; ii) one or more recombinant viruses; iii) one or more virus like particles; iv) one or more defective virus particles; and v) one or more nucleic acids encoding the antigen. The vaccine can comprise H3, N8, H7 or N7-type influenza virus antigens from more than one virus isolate. The vaccine comprises at least one antigen from an H3, N8, H7 or N7-type influenza virus. The vaccine can be administered subcutaneously, intramuscularly, intradermally, transdermally, ocularly, mucosally, or orally. The vaccine can be administered intranasally. The vaccine can be administered to the feline one or more times. The vaccine can be administered in combination with at least one vaccine selected from the group consisting of a rhinotracheitis vaccine, calicivirus vaccine, panleukopenia vaccine, Chlamydia vaccine, bordetella vaccine, feline immunodeficiency virus vaccine, feline leukemia vaccine or rabies virus vaccine.

Another embodiment of the invention is directed to a method for protecting a feline from respiratory lesions caused by influenza virus, wherein the method comprises administering to the feline a therapeutically effective amount of a vaccine comprising: i) at least one H3, N8, H7 or N7-type influenza virus antigen, and ii) at least one pharmaceutically acceptable excipient. The vaccine can be administered to the feline before the feline is infected with the influenza virus. This method can comprise protecting the feline from lung lesions caused by the influenza virus.

Another embodiment of the invention is directed to a method for protecting a feline from having influenza virus in nasal or oral secretion caused by influenza virus infection, wherein the method comprises administering to the feline a therapeutically effective amount of a vaccine comprising: i) at least one H3, N8, H7 or N7-type influenza virus antigen, and ii) at least one pharmaceutically acceptable excipient. The vaccine can be administered to the feline before the feline is infected with the influenza virus.

Another embodiment of the invention is directed to a feline influenza vaccine, wherein the vaccine comprises: i) a therapeutically effective amount of at least one H3, N8, H7 or N7-type influenza virus antigen, and ii) at least one pharmaceutically acceptable excipient. The virus antigen(s) can comprise one or more inactivated viruses. The virus antigen(s) can comprise one or more from the group consisting of i) one or more live attenuated viruses; ii) one or more recombinant viruses; iii) one or more virus like particles; iv) one or more defective virus particles; and v) one or more nucleic acids encoding the antigen.

Another embodiment of the invention is directed to a kit for protecting a feline from influenza virus infection, wherein the kit comprises: a therapeutically effective amount of a vaccine that comprises at least one H3, N8, H7 or N7-type influenza virus antigen, and at least one component selected from the group consisting of:
  an apparatus for administering the vaccine to the feline,
  a pharmaceutically acceptable excipient that aids in administering the vaccine to the feline,
  a pharmaceutically acceptable excipient that enhances the feline's immune response to the vaccine,
  a food to be consumed by the feline simultaneously with the vaccine, and
  a treat to be consumed by the feline simultaneously with the vaccine.

The kit can comprise an apparatus for administering the vaccine to the feline subcutaneously, intramuscularly, intradermally, transdermally, ocularly, mucosally, or orally. The kit can comprise an apparatus for intranasally administering the vaccine to the feline.

Another embodiment of the invention is directed to a method of preventing the spread of influenza virus from a feline to one or more other animals, comprising administering to the feline an influenza vaccine comprising an H3, N8, H7 or N7-type influenza virus antigen. The one or more other animals can include (without limitation) canines, equines, humans, other felines, or birds.

Another embodiment of the invention is directed to a method of diagnosing a feline for influenza comprising determining the antibody titer using a hemagglutination inhibition (HI) assay or using an Enzyme-linked immunosorbent assay (ELISA).

Further benefits of Applicants' invention will be apparent to one skilled in the art from reading this specification.

DETAILED DESCRIPTION OF PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

As used herein, the term "feline" refers to any member of the Felidae family. Members of this family include wild, zoo, and domestic members, such as any member of the subfamilies Felinae, Panterinae or Acinonychinae. Nonlimiting examples of species included within the Felidae family are cats, lions, tigers, pumas, jaguars, leopards, snow leopards, panthers, North American mountain lions, cheetahs, lynx, bobcats, caracals or any cross breeds thereof. Cats also include domestic cats, pure-bred and/or mongrel companion cats, show cats, laboratory cats, cloned cats and wild or feral cats.

As used herein, "canine" refers to any member of the canidae family. Non-limiting examples of such members include all breeds of domestic dogs, wild dogs, wolves, foxes, coyotes, jackals, dingos, hyenas, dholes, culpeos, and fennecs.

As used herein, "equine" refers to any member of the equidae family. Non-limiting examples of such members include wild horses, all breeds of domestic horses, donkeys, wild assess, domestic assess, onagers, khurs, kiangs, zebras, and quaggas.

As used herein, "protecting" a feline from an influenza virus infection includes, without limitation, preventing infection within an individual feline, preventing spread of infection from one feline to one or more other felines or other species, reducing the risk of influenza virus infection within an individual feline, reducing the risk of spread of influenza virus infection from one feline to one or more other felines or other species, delaying the onset of influenza virus infection within an individual feline, delaying the onset of spread of influenza virus infection from one feline to one or more other felines or other species, suppressing influenza virus infection in an individual feline, suppressing spread of influenza virus infection from one feline to one or more other felines or other species, ameliorating influenza virus infection in an individual feline, ameliorating the spread of influenza virus infection from one feline to one or more other felines or other species, attenuating influenza virus infection within an individual feline, attenuating the spread of influenza virus infection from one feline to one or more other felines or other species, eradicating an influenza virus infection within an individual feline, or eradicating the spread of influenza virus infection from one feline to one or more other felines or other species. Non-limiting examples of other species include humans, equines, canines, and poultry.

As used herein, feline flu refers to influenza caused flu in felines. Feline flu as used herein does not refer to flu caused by feline herpes virus or feline calicivirus.

As used herein, an influenza virus antigen includes one or more proteins or peptides or one or more nucleic acids from an H3, H7, N8 or N7 influenza virus (e.g., H3N8 or H7N7). An influenza virus antigen can also include whole or partial influenza virus virions, or influenza virus like particles from an H3, H7, N8 or N7 influenza virus.

As used herein, an "H3 influenza virus" or "H3-type influenza virus" includes any influenza strain in which its hemagglutinin protein is classified as belonging to H3, regardless of the classes to which its other proteins belong (e.g., H3N8). As used herein, an "H7 influenza virus" or "H7-type influenza virus" includes any influenza strain in which its hemagglutinin protein is classified as belonging to H7, regardless of the classes to which its other proteins belong (e.g., H7N7). As used herein, an "N8 influenza virus" or "N8-type influenza virus" includes any influenza strain in which its neuraminidase protein is classified as belonging to N8 (e.g., H3N8). As used herein, an "N7 influenza virus" or "N7-type influenza virus"[9] includes any influenza strain in which its neuraminidase protein is classified as belonging to N7 (e.g., H7N7). An antigen from an H3, H7, N8 or N7 influenza virus can be any antigen from the associated H3, H7, N8 or N7 type influenza virus. Such an antigen can be the hemagglutinin or neuraminidase proteins (or epitopic regions thereof) or other proteins contained within the influenza. Antigens of H3, H7, N8 or N7-type influenza viruses include the whole or part of the influenza virus as well as hemagglutinin, neuraminidase or other influenza virus proteins or biological structures.

Particular antigens of influenza virus strain A/canine/Florida/43/2004 show significant homology with the sequences of other known canine influenza viruses, equine influenza viruses, H3- or H7-type influenza viruses and N8- or N7-type influenza viruses. Table 1 illustrates the similarities among the amino acid sequences encoded by the hemagglutinin (or "HA"), neuraminidase (or "NA"), and nucleoprotein (NP) genes of the canine influenza virus identified as A/canine/Florida/43/2004 with other H3N8 equine isolates (including the A/canine/Florida/242/2003 isolate). Any of the strains described in table 1 are useful as feline vaccines according to the present invention.

TABLE 1

Hemagglutinin, neuraminidase and nucleoprotein gene amino acid sequence similarities among influenza viruses

| Gene (A/Canine/Florida/43/2004) | Amino acid sequence similarity | Gene of influenza virus used for comparison |
| --- | --- | --- |
| Hemagglutinin (HA) | 88 | equine/Algiers/72 |
| HA | 90 | equine/Sao paulo/6/69 |
| HA | 91 | equine/Miami/1/63 |
| HA | 93 | equine/Newmarket/79 |
| HA | 94 | equine/Kentucky/1/81 |
| HA | 95 | Equi-2/Ludhiana/87 |
| HA | 96 | Equine/Alaska/1/91 |
| HA | 97 | equine/Tennessee/5/86 |
| HA | 98 | equine/Kentucky/5/02 |
| HA | 99 | equine/Ohio/1/2003 |
| HA | 99 | A/canine/Florida/242/2003 |
| Neuraminidase (NA) | 88 | Eq/Algiers/72 |
| NA | 90 | equine/Sao Paulo/6/69 |
| NA | 91 | equine/Miami/1/63 |
| NA | 93 | equine/Newmarket/79 |
| NA | 94 | equine/Kentucky/1/81 |
| NA | 95 | Equi-2/Ludhiana/87 |
| NA | 96 | equine/Santiago/85 |
| NA | 97 | equine/Tennessee/5/86 |
| NA | 98 | equine/Kentucky/5/2002 |
| NA | 99 | equine/Ohio/1/2003 |
| NA | 99 | A/canine/Florida/242/2003 |
| Nucleoprotein (NP) | 94 | equi/Miami/1/63 |
| NP | 97 | equine/Kentucky/1/81 |
| NP | 99 | equine/Kentucky/5/02 |
| NP | 99 | equine/Ohio/1/2003 |
| NP | 99 | A/canine/Florida/242/2003 |

Other examples of H3 influenza viruses (or parts thereof) that can be used according to the invention include, without limitation, equine-2/Kentucky/93, equine-1/Pennsylvania/63, equine/Wisconsin/03, equine/Kentucky/02, equine/Kentucky/93, and equine/New Market 2/93. Examples of other H3 influenza viruses that can be used according to the invention include, without limitation, those described in U.S. Pat. Nos. 6,177,082, 6,398,774 or 6,436,408, which are all hereby incorporated by reference in their entirety. U.S. patent application Ser. No. 11/409,416, filed Apr. 21, 2006 and international patent application no. PCT/US2006/015090, filed Apr. 21, 2006 (published as WO06/116082), both of which are herein incorporated by reference in their entirety, also describe H3, H7, N8 or N7-type influenza viruses that are useful according to the present invention.

It is believed, however, that other H3, H7, N8 or N7-type influenza viruses may be used in accordance with this invention.

It is believed that HA induces an antibody response, and NA induces a cellular response.

In accordance with this invention, a feline may be immunized with one or more inactivated (i.e., killed) and/or live attenuated influenza virus vaccines or vaccines comprising a multiplicity of influenza virus antigens from one or more virus isolates.

An example of an inactivated vaccine useful according to the present invention is the EQUICINE II™ vaccine, which has been marketed by Intervet Inc. (Millsboro, Del., USA) as a liquid vaccine. EQUICINE II™ vaccine contains inactivated A/Pennsylvania/63 influenza virus ("A/Pa/63") and A/equine/Kentucky/93 influenza virus ("A/KY/93") with carbopol (i.e., HAVLOGEN® adjuvant (Intervet Inc.)).

Another example of an inactivated vaccine useful according to the present invention is equine flu virus A/equine/Ohio/03 ("Ohio 03"). In some embodiments, such a vaccine contains CARBIGEN™ adjuvant, which is an emulsified polymer-based adjuvant commercially available from MVP Laboratories, Inc. (Ralston, Nebr.). In such vaccines, a dosage unit typically comprises at least about 250 HA units of the virus, from about 250 to about 12,500 HA units of the virus, or from about 1000 to about 6200 HA units of the virus. The recommended concentration of CARBIGEN™ adjuvant is from about 5 to about 30% (by mass).

Live attenuated vaccines may be prepared by conventional means. Such means generally include, for example, modifying pathogenic strains by in vitro passaging, cold adaptation, modifying the pathogenicity of the organism by genetic manipulation, preparation of chimeras, insertion of antigens into viral vectors, selecting non-virulent wild type strains, and other methods well known to the skilled artisan.

In some embodiments, the live attenuated virus strain is derived by serial passage of the wild-type virus through cell culture, laboratory animals, non-host animals, or eggs. The accumulation of genetic mutation during such passage(s) typically leads to progressive loss of virulence of the organism to the original host.

In some embodiments, the live attenuated virus strain is prepared by co-infection of permissible cells with an attenuated mutant virus and pathogenic virus. The desired resultant recombinant virus has the safety of the attenuated virus with genes coding for protective antigens from the pathogenic virus.

In some embodiments, the live attenuated virus strain is prepared by cold adaptation. A cold-adapted virus has an advantage of replicating only at the temperature found in upper respiratory tract. A method of generation of a cold-adapted equine influenza virus has been described in U.S. Pat. No. 6,177,082 (hereby incorporated by reference in its entirety). A desired resulting cold-adapted virus confers one or more of the following phenotypes: cold adaptation, temperature sensitivity, dominant interference, and or attenuation.

In some embodiments, the live attenuated virus strain is prepared by molecular means, such as point mutation, deletion, or insertion to convert a pathogenic virus to a non-pathogenic or less-pathogenic virus compared to the original virus, while preserving the protective properties of the original virus.

In some embodiments, the live attenuated virus is prepared by cloning the candidate of genes of protective antigens into a genome of a non-pathogenic or less-pathogenic influenza or other, virus or other organism.

Inactivated (i.e., "killed") virus vaccines may be prepared by inactivating the virus using conventional methods. Typically, such vaccines include excipients that may enhance an immune response, as well as other excipients that are conventionally used in vaccines. For example, in the examples that follow, EQUICINE II™ vaccine comprises HAVLOGEN® adjuvant. Inactivation of the virus can be accomplished by treating the virus with inactivation chemicals (e.g., formalin, beta propiolactone ("BPL"), bromoethylamine ("BEA"), and binary ethylenimine ("BEI")) or by non-chemical methods (e.g., heat, freeze/thaw, or sonication) to disable or decrease the replication capacity of the virus.

In general, the vaccine is administered in a therapeutically effective amount. A "therapeutically effective amount" is an amount sufficient to induce a protective response in the feline patient against the target virus. Typically, a dosage is "therapeutically effective" if it prevents, reduces the risk of, delays the onset of, reduces the spread of, ameliorates, suppresses, or eradicates the influenza or one or more (typically two or more) of its symptoms. Typical influenza symptoms include, for example, fever (for cats, typically $\geqq$103.0° F.; $\geqq$39.4° C.), cough, sneezing, histopathological lesions, ocular discharge, nasal discharge, vomiting, diarrhea, depression, weight loss, gagging, hemoptysis, and/or audible rates. Other often more severe symptoms may include, for example, hemorrhage in the lungs, mediastanum, or pleural cavity; tracheitis; bronchitis; bronchiolitis; supportive bronchopneumonia; and/or infiltration of the epithelial lining and airway lumens of the lungs with neutrophils and/or macrophages.

The vaccine may be administered as part of a combination therapy, i.e., a therapy that includes, in addition to the vaccine itself, administering one or more additional active agents, adjuvants, therapies, etc. In that instance, it should be recognized the amount of vaccine that constitutes a "therapeutically effective" amount may be more or less than the amount of vaccine that would constitute a "therapeutically effective" amount if the vaccine were to be administered alone. Other therapies may include those known in the art, such as, for example, anti-viral medications, analgesics, fever-reducing medications, expectorants, anti-inflammation medications, antihistamines, antibiotics to treat bacterial infection that results from the influenza virus infection, rest, and/or administration of fluids. In some embodiments, the vaccine of this invention is administered in combination with a rhinotracheitis vaccine, calicivirus vaccine, panleukopenia vaccine, Chlamydia vaccine, bordetella vaccine, immunodeficiency virus vaccine, leukemia virus vaccine or rabies vaccine.

In some embodiments, for example, a typical dose for a live attenuated vaccine is at or above about $10^3$ pfu/feline, and more typically from about $10^3$ to about $10^9$ pfu/feline. In this patent, "pfu" means "plaque forming units". In some embodiments, a typical dose for a live attenuated vaccine is at or above about $10^3$ $TCID_{50}$/feline, and more typically from about $10^3$ to about $10^9$ $TCID_{50}$/feline. In some embodiments, a typical dose for a live attenuated vaccine is at or above about $10^3$ $EID_{50}$/feline, and more typically from about $10^3$ to about $10^9$ $EID_{50}$/feline. In some embodiments, a typical dose for a killed vaccine is at or above about 40 HA units, typically from about 40 to about 10,000 HA units, and more typically from about 500 to about 6200 HA units. In some embodiments, the dose is from about 6100 to about 6200 HA units.

In some preferred embodiments, the vaccine comprises a live attenuated vaccine at a concentration which is at least about $10^{0.5}$ pfu/feline greater than the immunogenicity level. In some preferred embodiments, the vaccine comprises a live attenuated vaccine at a concentration which is at least about $10^{0.5}$ $TCID_{50}$/feline greater than the immunogenicity level. In some preferred embodiments, the vaccine comprises a live attenuated vaccine at a concentration which is at least about $10^{0.5}$ $EID_{50}$/feline greater than the immunogenicity level.

The immunogenicity level may be determined experimentally by challenge dose titration study techniques generally known in the art. Such techniques typically include vaccinating a number of felines with the vaccine at different dosages, and then challenging the felines with the virulent virus to determine the minimum protective dose.

Factors affecting the preferred dosage regimen may include, for example, the type (e.g., species and breed), age, weight, sex, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art using conventional means. It should further be noted that live attenuated viruses are generally self-propagating; thus, the specific amount of such a virus administered is not necessarily critical.

It is contemplated that the vaccine may be administered to the feline patient a single time; or, alternatively, two or more times over days, weeks, months, or years. In some embodiments, the vaccine is administered at least two times. In some such embodiments, for example, the vaccine is administered twice, with the second dose (e.g., the booster) being administered at least about 2 weeks after the first. In some embodiments, the vaccine is administered twice, with the second dose being administered no greater than 8 weeks after the first. In some embodiments, the second dose is administered at from about 2 weeks to about 4 years after the first dose, from about 2 to about 8 weeks after the first dose, or from about 3 to about 4 weeks after the first dose. In some embodiments, the second dose is administered about 4 weeks after the first dose. In the above embodiments, the first and subsequent dosages may vary, such as, for example, in amount and/or form. Often, however, the dosages are the same as to amount and form. When only a single dose is administered, the amount of vaccine in that dose alone generally comprises a therapeutically effective amount of the vaccine. When, however, more than one dose is administered, the amounts of vaccine in those doses together may constitute a therapeutically effective amount.

In some embodiments, the vaccine is administered before the feline recipient is infected with influenza. In such embodiments, the vaccine may, for example, be administered to prevent, reduce the risk of, or delay the onset of influenza or one or more (typically two or more) influenza symptoms.

In some embodiments, the vaccine is administered after the feline recipient is infected with influenza. In such embodiments, the vaccine may, for example, ameliorate, suppress, or eradicate the influenza or one or more (typically two or more) influenza symptoms.

The preferred composition of the vaccine depends on, for example, whether the vaccine is an inactivated vaccine, live attenuated vaccine, or both. It also depends on the method of administration of the vaccine. It is contemplated that the vaccine will comprise one or more conventional pharmaceutically acceptable carriers, adjuvants, other immune-response enhancers, and/or vehicles (collectively referred to as "excipients"). Such excipients are generally selected to be compatible with the active ingredient(s) in the vaccine. Use of excipients is generally known to those skilled in the art.

The term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient canine.

The vaccines may be administered by conventional means, including, for example, mucosal administration, (such as intranasal, oral, intratracheal, and ocular), and parenteral administration (such as, without limitation, subcutaneous or intramuscular administration). The vaccines may also be administered intradermally or transdermally (including, without limitation, via a skin patch or topical administration). Mucosal administration is often particularly advantageous for live attenuated vaccines. Parenteral administration is often particularly advantageous for inactivated vaccines.

Mucosal vaccines may be, for example, liquid dosage forms, such as pharmaceutically acceptable emulsions, solutions, suspensions, syrups, and elixirs. Excipients suitable for such vaccines include, for example, inert diluents commonly used in the art, such as, water, saline, dextrose, glycerol, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol. Excipients also can comprise various wetting, emulsifying, suspending, flavoring (e.g., sweetening), and/or perfuming agents.

Oral mucosal vaccines also may, for example, be tableted or encapsulated for convenient administration. Such capsules or tablets can contain a controlled-release formulation. In the case of capsules, tablets, and pills, the dosage forms also can comprise buffering agents, such as sodium citrate, or magnesium or calcium carbonate or bicarbonate. Tablets and pills additionally can be prepared with enteric coatings.

It is contemplated that the vaccine may be administered via the feline patients drinking water and/or food. It is further contemplated that the vaccine may be administered in the form of a treat or toy.

"Parenteral administration" includes subcutaneous injections, submucosal injections, intravenous injections, intramuscular injections, intrasternal injections, and infusion. Injectable preparations (e.g., sterile injectable aqueous or oleaginous suspensions) can be formulated according to the known art using suitable excipients, such as vehicles, solvents, dispersing, wetting agents, emulsifying agents, and/or suspending agents. These typically include, for example, water, saline, dextrose, glycerol, ethanol, corn oil, cottonseed oil, peanut oil, sesame oil, benzyl alcohol, benzyl alcohol, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), propylene glycol, and/or polyethylene glycols. Excipients also may include small amounts of other auxiliary substances, such as pH buffering agents.

The vaccine may include one or more excipients that enhance a feline patient's immune response (which may include an antibody response, cellular response, or both), thereby increasing the effectiveness of the vaccine. Use of such excipients (or "adjuvants") may be particularly beneficial when using an inactivated vaccine. The adjuvant(s) may be a substance that has a direct (e.g., cytokine or Bacillé Calmette-Guerin ("BCG")) or indirect effect (liposomes) on cells of the feline patients immune system. Examples of often suitable adjuvants include oils (e.g., mineral oils), metallic salts (e.g., aluminum hydroxide or aluminum phosphate), bacterial components (e.g., bacterial liposaccharides, Freund's adjuvants, and/or MDP), plant components (e.g., Quil A), and/or one or more substances that have a carrier effect (e.g., bentonite, latex particles, liposomes, and/or Quil A, ISCOM). As noted above, adjuvants also include, for example, CARBIGEN™ adjuvant and carbopol. It should be recognized that this invention encompasses both vaccines that comprise an adjuvant(s), as well as vaccines that do not comprise any adjuvant.

It is contemplated that the vaccine may be freeze-dried (or otherwise reduced in liquid volume) for storage, and then reconstituted in a liquid before or at the time of administration. Such reconstitution may be achieved using, for example, vaccine-grade water.

The present invention further comprises kits that are suitable for use in performing the methods described above. The kit comprises a dosage form comprising a vaccine described above. The kit also comprises at least one additional component, and, typically, instructions for using the vaccine with the additional component(s). The additional component(s) may, for example, be one or more additional ingredients (such as, for example, one or more of the excipients discussed above, food, and/or a treat) that can be mixed with the vaccine before or during administration. The additional component(s) may alternatively (or additionally) comprise one or more apparatuses for administering the vaccine to the feline patient. Such an apparatus may be, for example, a syringe, inhaler, nebulizer, pipette, forceps, or any medically acceptable delivery vehicle. In some embodiments, the apparatus is suitable for subcutaneous administration of the vaccine. In some embodiments, the apparatus is suitable for intranasal administration of the vaccine.

Other excipients and modes of administration known in the pharmaceutical or biologics arts also may be used.

EXAMPLES

The following examples are merely illustrative, and not limiting to the remainder of this disclosure in any way.

In the examples that follow, A/Canine/Florida/242/2003 was used as a challenge virus. It is known to have about 99% homology with A/canine/Florida/43/2004 isolates (see Table 1), and has been shown to induce symptoms of infection and seroconversion in cats. Example 2 illustrates the efficacy of a canine influenza vaccine in cats, showing hemagglutination inhibition (or "HI" or "HAI") titers in cats vaccinated with inactivated A/canine/Florida/43/2004 antigen in a vaccine composition comprising CARBIGEN™ adjuvant. Table 7 shows titers pre-vaccination, post-vaccination, and post-second vaccination, as well as post-challenge. The results indicate HI titers at each stage post-vaccination for the vaccinated cats, with little or no increase for controls. Table 8 illustrates the virus isolation results from the same study. Although challenged animals did not show clinical signs, virus shedding, or positive histopathology, the positive HI titers (Table 7) indicate significant antibody titers in immunized animals.

It should be noted that other canine influenza virus antigen vaccines, equine influenza virus antigen vaccines, H3 or N8 influenza virus antigen vaccines are encompassed by this invention as well. Non-limiting examples of other influenza virus antigens useful according to the present invention are derives from the virus strains shown in Table 1. Those described in this specification and the following examples are provided to illustrate the invention and its preferred embodiments, and not to limit the scope of the invention claimed.

It should further be noted that influenza antigens other than H3 influenza virus antigens may be used in accordance with this invention. Such antigens include without limitation, for example, those from equine/PA/63, which is an equine A1 subtype (H7N7). It is contemplated that one or more of such antigens may be used with or without one or more H3 influenza antigens.

Example 1

Feline Influenza Challenge Model Development

This example illustrates that felines are susceptible to H3N8 influenza viruses, and establishes a challenge model useful for measuring the efficacy of a feline influenza vaccine.

Procedure: Fourteen 13-week-old cats purchased from a commercial supplier were randomly assigned to 4 groups (Table 2). At 14 weeks-of-age, cats in Group 1 and 2 were challenged with an embryonated-chicken-egg grown canine influenza (A/Canine/Florida/242/2003) virus. Each cat received a total of approximately $10^{7.0}$ TCID$_{50}$ of virus in a 2 ml volume. For mock challenge, the cats were challenged with 2 ml of virus-free allantoic fluid.

For intratracheal challenge, 2 ml of the challenge virus (Group 1) or virus-free allantoic fluid (Group 3) was administered into the trachea first followed by 2 ml of PBS using a delivery tube, which consisted of a cuffed tracheal tube (Size 2.5, Rusch, Teleflex Medical, USA) and feeding tube (size 5 Fr, 1.7 mm,/16 inches in length, Kendall, USA).

For oronasal challenge, 2 ml of challenge virus (Group 2) or 2 ml of virus-free allantoic fluid (Group 4) was administered as a mist using a nebulizer. The cats were observed for flu-related clinical signs for 16 days post-challenge. All cats were fed with a standard growth diet and water was available ad libitum.

For virus isolation, nasal and oropharyngeal swabs were collected daily in tubes containing 2 ml of virus transport medium from day −2 (i.e., two day before challenge) through day 14 post-challenge. Blood samples were collected on day 0 (prior to challenge), and days 7 and 14 post-challenge for canine influenza virus antibody titer determination using a hemagglutination inhibition (HI) assay as described in SAM 124 (USDA, Ames, Iowa) with minor modification (canine influenza virus instead of equine influenza virus) and by Enzyme-linked immunosorbent assay (ELISA). Post-challenge clinical signs were recorded daily. Cats were observed for clinical signs from days 1-14. At the completion of the study, all cats were euthanized and tissue samples were collected for histopathological evaluation.

Results: Except a few sporadic cases of elevated body temperatures ($\geqq 103°$ F.), no influenza related signs were observed following virus challenge by either method of challenge. Following the challenge, 1 of 5 cats challenged intratracheally and 0 of 5 cats challenged oronasally had a measurable HI titer, as shown in Table 3. Whereas by ELISA method, 4 of 5 cats intratracheal challenge group (Group 1) and 5 of 5 cats from the oronasal challenge group (Group 2) had a titer greater than the mock challenge group (<400), as shown in Table 3.

Virus isolation results are shown in Tables 4 and 5. Following a virulent canine influenza virus challenge, the canine influenza virus was isolated from 1 of 5 (20%) cats from Group 1 (intratracheal), and 5 of 5 (100%) cats from Group 2 (oro-nasal). No virus was isolated from cats in either Group 3 or Group 4. There was a significant difference (P=0.048) in percent of cats excreting the virus (virus isolation) between intratracheal and oro-nasal route of challenge (20% vs. 100%).

Conclusion: The results from this study demonstrate that: 1) following the exposure of cats to a H3N8 influenza virus, cats developed anti-H3N8 influenza virus antibody which was measurable by a highly sensitive ELISA assay, 2) cats were susceptible to H3N8 influenza virus infection and excreted the challenge virus in nasal/oral secretions 1 to 4 days following the challenge, and 3) the route of challenge (oro-nasal vs. intratracheal) has a significant (P=0.048) influence on virus shedding.

TABLE 2

Experimental design

| Group | Treatment | Number of cats | Challenge material | Challenge route |
|---|---|---|---|---|
| 1 | Challenge | 5 | Challenge virus | Intratracheal |
| 2 | Challenge | 5 | Challenge virus | Oro-nasal |
| 3 | Mock-challenge | 2 | Virus-free allantoic fluid | Intratracheal |
| 4 | Mock-challenge | 2 | Virus-free allantoic fluid | Oro-nasal |

TABLE 3

Serology - antibody titer

| Cat ID | Group | Treatment | HI titer Pre-chall | HI titer 1 wk post chall | HI titer 2 wk post chall | ELISA titer Pre-chall | ELISA titer 1 wk post chall | ELISA titer 2 wk post chall |
|---|---|---|---|---|---|---|---|---|
| AUF2 | 1 | intratracheal | <10 | <10 | <10 | <400 | <400 | <800 |
| AUF3 | 1 | intratracheal | <10 | <10 | <10 | <400 | <400 | 25600 |
| AUG1 | 1 | intratracheal | <10 | <10 | <10 | <400 | <400 | 3200 |
| AUG3 | 1 | intratracheal | <10 | <10 | <10 | <400 | <400 | 51200 |
| QVO3 | 1 | intratracheal | <10 | <10 | 40 | <400 | <400 | 25600 |
| AUG2 | 2 | Oro-nasal | <10 | <10 | <10 | <400 | <400 | 25600 |
| QVN1 | 2 | Oro-nasal | <10 | <10 | <10 | <400 | <400 | 12800 |
| QVN2 | 2 | Oro-nasal | <10 | <10 | <10 | <400 | <400 | 6400 |
| QVP2 | 2 | Oro-nasat | <10 | <10 | <10 | <400 | <400 | 12800 |
| QVP4 | 2 | Oro-nasal | <10 | <10 | <10 | <400 | <400 | 6400 |
| AUG4 | 3 | Mock challenge | <10 | <10 | <10 | <400 | <400 | <400 |
| QVN3 | 3 | Mock challenge | <10 | <10 | <10 | <400 | <400 | <400 |
| QVN4 | 4 | Mock challenge | <10 | <10 | <10 | <400 | <400 | <400 |
| QVN5 | 4 | Mock challenge | <10 | <10 | <10 | <400 | <400 | <400 |

TABLE 4

Virus shedding

| Group no | Cat ID | Treatment | -2 | -1 | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|---|
| 1 | AUF2 | intratracheal | N | N | N | N | N | N | N | N | N | N | N | N | N | N | N | N | N |
| 1 | AUF3 | intratracheal | N | N | N | N | N | N | N | N | N | N | N | N | N | N | N | N | N |
| 1 | AUG1 | intratracheal | N | N | N | N | N | N | N | N | N | N | N | N | N | N | N | N | N |
| 1 | AUG3 | intratracheal | N | N | N | N | P | N | N | N | N | N | N | N | N | N | N | N | N |
| 1 | QVO3 | intratracheal | N | N | N | N | N | N | N | N | N | N | N | N | N | N | N | N | N |
| 2 | AUG2 | Oro-nasal | N | N | N | N | P | P | N | N | N | N | N | N | N | N | N | N | N |
| 2 | QVN1 | Oro-nasal | N | N | N | N | P | N | N | P | N | N | N | N | N | N | N | N | N |
| 2 | QVN2 | Oro-nasal | N | N | N | N | P | N | N | N | P | N | N | N | N | N | N | N | N |
| 2 | QVP2 | Oro-nasal | N | N | N | N | P | N | N | P | N | N | N | N | N | N | N | N | N |
| 2 | QVP4 | Oro-nasal | N | N | N | N | P | P | N | P | P | N | N | N | N | N | N | N | N |
| 3 | AUG4 | Mock challenge | N | N | N | N | N | N | N | N | N | N | N | N | N | N | N | N | N |
| 3 | QVN3 | Mock challenge | N | N | N | N | N | N | N | N | N | N | N | N | N | N | N | N | N |
| 4 | QVN4 | Mock challenge | N | N | N | N | N | N | N | N | N | N | N | N | N | N | N | N | N |
| 4 | QVN5 | Mock challenge | N | N | N | N | N | N | N | N | N | N | N | N | N | N | N | N | N |

N - No virus isolated from oral or nasal swabs
P - Virus isolated from nasal or oral or nasal and oral swabs.

TABLE 5

Virus shedding summary

| Group | Challenge route | Challenge material | Percent virus shedding | P-value |
|---|---|---|---|---|
| 1 | Intratracheal | Challenge virus | 20% (1/5cats) | 0.048 |
| 2 | Oro-nasal | Challenge virus | 100% (5/5cats) | (Group 1 vs. 2) |
| 3 | Mock-challenge | Virus-free allantoic fluid | 0% (0/2) | — |
| 4 | Mock-challenge | Virus-free allantoic fluid | 0% (0/2) | — |

Example 2

Efficacy of H3N8 Virus Vaccine in Felines

In the following study, efficacy of an H3N8 virus vaccine in cats was determined.

Procedure: Twenty 7-week old cats purchased from a commercial supplier were randomly assigned to 2 groups (Table 6). At 8 and 12 weeks-of-age, 10 cats (Group 1) were vaccinated with an inactivated, CARBIGEN™ adjuvant adjuvanted, canine influenza virus (A/canine/Florida/43/2004) vaccine via subcutaneous route. For vaccine preparation, The A/canine/Florida/43/2004 virus was inactivated by binary ethylenimine ("BEI") using a standard method. Each dose of the vaccine contained 5% by mass CARBIGEN™ adjuvant, approximately 1280 HA units of the inactivated virus, sufficient PBS to bring the total volume of the dose to 1 ml, and sufficient NaOH to adjust the pH to between 7.2 and 7.4. Ten cats from Group 2 were sham-vaccinated with 1 ml of PBS via subcutaneous route. Serum samples were collected from all cats on the day of first and second vaccination, days 7 and 14 post first and second vaccinations to determine the HI titers using an H3N8 equine influenza virus standard protocol (Supplemental Assay Method (SAM) 124, CVB, USDA, Ames, Iowa). All cats were fed with a standard growth diet and water was available ad libitum.

TABLE 6

Experimental design

| Group | Treatment | Vaccination route | Number of cats | Age at vaccination (weeks) | Challenge |
|---|---|---|---|---|---|
| 1 | Vaccinate | SC | 10 | 8 & 12 | Yes |
| 2 | Control | N/A | 10 | N/A | Yes |

All vaccinates and age-matched control cats were challenged oronasally with a virulent canine influenza virus ($10^{7.2}$ $TCID_{50}$ of A/Canine/Florida/242/2003 per cat) at 2 weeks post second vaccination. The challenge virus was administered as a mist (2 ml/cat) using a nebulizer. The cats were observed for influenza-related clinical signs for 14 days post challenge. Nasal and oropharyngeal swabs were collected daily in tubes containing 2 ml of virus transport medium for virus isolation from day-2 (i.e., two day before challenge) through day 14 post-challenge. Blood samples were collected on days 7 and 14 post challenge for HI titer determination. Cats were observed for flu clinical signs from days 1-14. At the completion of the study, all cats were euthanized and tissue samples were collected for histopathological evaluation.

Results: Serum HI titer results are presented in Table 7. All vaccinated cats (Group 1) developed HI antibody titer to the inactivated canine influenza virus (H3N8) vaccine and all controls remain HI antibody (<10) negative prior to challenge. Following the challenge, a few sporadic cases of elevated body temperatures (≧103° F.) were observed both in vaccinated and control cats. No other influenza related signs were observed following the virus challenge.

During the post challenge observation period, 0 of 10 cats from Group 1 (vaccinates) and 8 of 10 cats from Group 2 (controls) excreted the virus in nasal secretion or oral secretion or both for 1 to 3 days during the first 7 days of post challenge (Table 8). Vaccination of cats with the canine influenza virus vaccine prevented the H3N8 virus shedding in 100% of the cats (Table 9).

Conclusion: The results from this study demonstrate that: 1) all vaccinated cats developed HI antibody following vaccination with the H3N8 type canine influenza virus vaccine, 2) following the challenge a minimum 2 fold increase in HI antibody titer was seen in all cats and 3) vaccination of cats with the canine influenza virus (H3N8) vaccine prevented canine influenza challenge virus shedding in 100% of the cats.

TABLE 7

Serology - HI antibody titer

| Group | | | Vaccination | HI titer | | | | | | | |
|---|---|---|---|---|---|---|---|---|---|---|---|
| | | | | Days post vaccination | | | | | | Days post challenge | |
| No | Cat ID | Treatment | route | 0* | 7 | 14 | 28** | 35 | 42*** | 7 | 14 |
| 1 | JCY2 | Vaccinate | SC | <10 | <10 | 10 | 20 | 80 | 160 | 320 | ≧640 |
| 1 | JCX1 | Vaccinate | SC | <10 | <10 | 10 | 20 | 40 | 40 | 80 | 80 |
| 1 | JCZ2 | Vaccinate | SC | <10 | <10 | <10 | 20 | 40 | 80 | 160 | 320 |
| 1 | JCZ3 | Vaccinate | SC | <10 | 10 | 10 | 40 | 80 | 160 | 320 | ≧640 |
| 1 | JCZ4 | Vaccinate | SC | <10 | <10 | 20 | 160 | 320 | 320 | ≧640 | ≧640 |
| 1 | JCZ5 | Vaccinate | SC | <10 | <10 | 10 | 40 | 80 | 80 | 160 | 320 |
| 1 | JCZ6 | Vaccinate | SC | <10 | <10 | 10 | 80 | 160 | 320 | ≧640 | ≧640 |
| 1 | JCZ7 | Vaccinate | SC | <10 | <10 | 10 | 40 | 160 | 160 | 320 | ≧640 |
| 1 | JDA2 | Vaccinate | SC | <10 | <10 | 10 | 40 | 80 | 80 | 160 | 320 |
| 1 | JDA3 | Vaccinate | SC | <10 | <10 | 10 | 20 | 80 | 160 | 160 | 320 |
| 2 | JDA4 | Control | N/A | <10 | <10 | <10 | <10 | <10 | <10 | <10 | 40 |
| 2 | JDA5 | Control | N/A | <10 | <10 | <10 | <10 | <10 | <10 | <10 | 20 |
| 2 | JCX2 | Control | N/A | <10 | <10 | <10 | <10 | <10 | <10 | <10 | 20 |
| 2 | JCX3 | Control | N/A | <10 | <10 | <10 | <10 | <10 | <10 | <10 | 40 |
| 2 | JCY1 | Control | N/A | <10 | <10 | <10 | <10 | <10 | <10 | <10 | 40 |
| 2 | JCY3 | Control | N/A | <10 | <10 | <10 | <10 | <10 | <10 | <10 | 20 |
| 2 | JCY4 | Control | N/A | <10 | <10 | <10 | <10 | <10 | <10 | <10 | 40 |
| 2 | JCY5 | Control | N/A | <10 | <10 | <10 | <10 | <10 | <10 | <10 | 40 |

TABLE 7-continued Serology - HI antibody titer

| Group | | | | HI titer | | | | | | |
|---|---|---|---|---|---|---|---|---|---|---|
| | | | | Days post vaccination | | | | | Days post challenge | |
| No | Cat ID | Treatment | Vaccination route | 0* | 7 | 14 | 28** | 35 | 42*** | 7 | 14 |
| 2 | JCY6 | Control | N/A | <10 | <10 | <10 | <10 | <10 | <10 | <10 | 40 |
| 2 | JCZ1 | Control | N/A | <10 | <10 | <10 | <10 | <10 | <10 | <10 | 40 |

*First vaccination;
**Second vaccination;
***Day of challenge

TABLE 8

Virus shedding

| Group | | | Days post challenge | | | | | | | | | | | | | | |
|---|---|---|---|---|---|---|---|---|---|---|---|---|---|---|---|---|---|
| No | Cat ID | Treatment | −2 | −1 | 0 | 1 | 2 | 3 | 4 | 5 | 6 | 7 | 8 | 9 | 10 | 11 | 12 | 13 | 14 |
| 1 | JCY2 | Vaccinate | N | N | N | N | N | N | N | N | N | N | N | N | N | N | N | N | N |
| 1 | JCX1 | Vaccinate | N | N | N | N | N | N | N | N | N | N | N | N | N | N | N | N | N |
| 1 | JCZ2 | Vaccinate | N | N | N | N | N | N | N | N | N | N | N | N | N | N | N | N | N |
| 1 | JCZ3 | Vaccinate | N | N | N | N | N | N | N | N | N | N | N | N | N | N | N | N | N |
| 1 | JCZ4 | Vaccinate | N | N | N | N | N | N | N | N | N | N | N | N | N | N | N | N | N |
| 1 | JCZ5 | Vaccinate | N | N | N | N | N | N | N | N | N | N | N | N | N | N | N | N | N |
| 1 | JCZ6 | Vaccinate | N | N | N | N | N | N | N | N | N | N | N | N | N | N | N | N | N |
| 1 | JCZ7 | Vaccinate | N | N | N | N | N | N | N | N | N | N | N | N | N | N | N | N | N |
| 1 | JDA2 | Vaccinate | N | N | N | N | N | N | N | N | N | N | N | N | N | N | N | N | N |
| 1 | JDA3 | Vaccinate | N | N | N | N | N | N | N | N | N | N | N | N | N | N | N | N | N |
| 2 | JDA4 | Control | N | N | N | N | N | N | N | N | N | N | N | N | N | N | N | N | N |
| 2 | JDA5 | Control | N | N | N | P | N | N | N | N | N | N | N | N | N | N | N | N | N |
| 2 | JCX2 | Control | N | N | N | N | N | N | N | P | N | N | N | N | N | N | N | N | N |
| 2 | JCX3 | Control | N | N | N | N | N | N | N | N | P | N | N | N | N | N | N | N | N |
| 2 | JCY1 | Control | N | N | N | N | P | N | N | P | P | N | N | N | N | N | N | N | N |
| 2 | JCY3 | Control | N | N | N | N | N | N | N | N | N | N | N | N | N | N | N | N | N |
| 2 | JCY4 | Control | N | N | N | N | P | N | P | P | N | N | N | N | N | N | N | N | N |
| 2 | JCY5 | Control | N | N | N | N | P | N | N | P | N | N | N | N | N | N | N | N | N |
| 2 | JCY6 | Control | N | N | N | N | P | N | N | N | N | N | N | N | N | N | N | N | N |
| 2 | JCZ1 | Control | N | N | N | N | P | N | N | N | P | N | N | N | N | N | N | N | N |

N - No virus isolated from oral or nasal swabs
P - Virus isolated from nasal or oral or nasal and oral swabs.

P—Virus isolated from nasal or oral or nasal and oral swabs.

TABLE 9

Virus shedding summary

| Group | Treatment | Percent virus shedding | P-value |
|---|---|---|---|
| 1 | Vaccinate | 0% (0/10 cats) | 0.0007 |
| 2 | Control | 80% (8/10 cats) | |

The words "comprise," "comprises," and "comprising" in this patent (including the claims) are to be interpreted inclusively rather than exclusively. This interpretation is intended to be the same as the interpretation that these words are given under United States patent law.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A method for inducing an immune response in a feline comprising administering to the feline an immunogenically effective amount of a composition comprising:
   i) at least one whole, inactivated H3N8 influenza virus and
   ii) at least one pharmaceutically acceptable excipient.

2. The method according to claim 1, wherein the composition comprises whole, inactivated H3N8 influenza virus from more than one virus isolate.

3. The method according to claim 1, wherein the composition is administered subcutaneously, intramuscularly, intradermally, transdermally, ocularly, mucosally, or orally.

4. The method according to claim 1, wherein the composition is administered intranasally.

5. The method according to claim 1, wherein the composition is administered to the feline one or more times.

6. The method according to claim 1, wherein the composition is administered in combination with at least one antigen of a feline pathogen selected from the group consisting of a rhinotracheitis virus, calicivirus, panleukopenia virus, Chlamydia, bordetella, feline immunodeficiency virus, feline leukemia virus and rabies virus.

* * * * *